United States Patent
Biedermann et al.

(10) Patent No.: US 11,896,275 B2
(45) Date of Patent: *Feb. 13, 2024

(54) DYNAMIC BONE ANCHOR AND METHOD OF MANUFACTURING A DYNAMIC BONE ANCHOR

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 17/334,387

(22) Filed: May 28, 2021

(65) Prior Publication Data

US 2021/0353342 A1    Nov. 18, 2021

Related U.S. Application Data

(63) Continuation of application No. 14/098,425, filed on Dec. 5, 2013, now Pat. No. 11,045,237.

(Continued)

(30) Foreign Application Priority Data

Dec. 5, 2012   (EP) .................................... 12195759

(51) Int. Cl.
*A61B 17/84*   (2006.01)
*A61B 17/86*   (2006.01)
(Continued)

(52) U.S. Cl.
CPC .......... *A61B 17/844* (2013.01); *A61B 17/866* (2013.01); *A61B 17/8625* (2013.01);
(Continued)

(58) Field of Classification Search
CPC . A61B 17/844; A61B 17/8625; A61B 17/866; A61B 17/8685; A61B 17/864;
(Continued)

(56) References Cited

U.S. PATENT DOCUMENTS

| | | |
|---|---|---|
| 4,870,957 A | 10/1989 | Goble et al. |
| 5,061,137 A | 10/1991 | Gourd |

(Continued)

FOREIGN PATENT DOCUMENTS

| | | |
|---|---|---|
| CN | 2453859 Y | 10/2001 |
| EP | 1 743 587 A1 | 1/2007 |

(Continued)

OTHER PUBLICATIONS

Chinese OA for Application No. 201310632148.2, dated Jan. 3, 2017 and English translation (21 pages).

(Continued)

*Primary Examiner* — Si Ming Ku
*Assistant Examiner* — Tracy L Kamikawa
(74) *Attorney, Agent, or Firm* — Lewis Roca Rothgerber Christie LLP

(57) ABSTRACT

A dynamic bone anchor includes an anchor member having a tubular body with a first end and a second end, the anchor member defining an anchor axis including a plurality of barb elements, and being made at least partially of a nickel-titanium (Ni—Ti) based shape memory alloy. The dynamic bone anchor also including a core member configured to be inserted from the first end through the second end such that a first portion of the core number extends out from the first end, and a second portion of the core number extends out (Continued)

from the second end. The anchor member and the core member are configured such that when assembled, the first portion of the core member is spaced apart from the anchor member and movable with respect to it, and the second portion of the core member is fixed to and movable together with the anchor member.

20 Claims, 7 Drawing Sheets

Related U.S. Application Data

(60) Provisional application No. 61/733,793, filed on Dec. 5, 2012.

(51) Int. Cl.
   *A61B 17/70* (2006.01)
   *A61B 17/00* (2006.01)

(52) U.S. Cl.
   CPC ...... *A61B 17/8685* (2013.01); *A61B 17/7035* (2013.01); *A61B 2017/00862* (2013.01); *A61B 2017/8655* (2013.01); *F04C 2270/0421* (2013.01); *Y10T 29/49826* (2015.01)

(58) Field of Classification Search
   CPC ... A61B 17/86; A61B 17/7035; A61B 17/704; A61B 2017/8655; A61B 2017/00867
   See application file for complete search history.

(56) References Cited

U.S. PATENT DOCUMENTS

| | | | |
|---|---|---|---|
| 5,169,400 A | 12/1992 | Muhling et al. | |
| 5,584,695 A * | 12/1996 | Lal Sachdeva | A61C 8/0065 433/173 |
| 5,876,434 A | 3/1999 | Flomenblit et al. | |
| 6,887,276 B2 * | 5/2005 | Gerbec | A61F 2/38 623/19.12 |
| 7,235,079 B2 | 6/2007 | Jensen et al. | |
| 7,879,036 B2 * | 2/2011 | Biedermann | A61B 17/8685 606/279 |
| 8,292,932 B2 | 10/2012 | Matthis et al. | |
| 2006/0264954 A1 | 11/2006 | Sweeney, II et al. | |
| 2007/0293866 A1 | 12/2007 | Stoeckel et al. | |
| 2008/0294204 A1 | 11/2008 | Chirico et al. | |
| 2009/0131992 A1 | 5/2009 | Greenhalgh et al. | |
| 2009/0157123 A1 * | 6/2009 | Appenzeller | A61B 17/68 606/301 |
| 2010/0076498 A1 | 3/2010 | Tyber et al. | |
| 2010/0228301 A1 | 9/2010 | Greenhalgh et al. | |
| 2010/0261034 A1 | 10/2010 | Cardarelli | |
| 2011/0202096 A1 | 8/2011 | White et al. | |
| 2011/0213425 A1 * | 9/2011 | Keren | A61B 17/8033 606/305 |
| 2012/0184993 A1 | 7/2012 | Arambula et al. | |
| 2012/0245704 A1 | 9/2012 | Childs | |
| 2012/0295129 A1 | 11/2012 | Kato et al. | |
| 2013/0116694 A1 * | 5/2013 | Zurschmiede | A61B 17/742 606/65 |
| 2013/0245697 A1 | 9/2013 | Hulliger | |
| 2014/0172027 A1 | 6/2014 | Biedermann et al. | |

FOREIGN PATENT DOCUMENTS

| | | |
|---|---|---|
| JP | 2005-516721 A | 6/2005 |
| JP | 2014-113486 A | 6/2014 |
| WO | WO 03/068083 A1 | 8/2003 |
| WO | WO 2007/101267 A1 | 9/2007 |
| WO | WO 2009/059227 A1 | 5/2009 |
| WO | WO 2011/092909 A1 | 8/2011 |

OTHER PUBLICATIONS

EP Office action for Application No. 12 195 759.1, dated Jun. 1, 2015 (5 sheets).
Extended European Search Report for European Application No. 12195759.1, European Search Report dated Apr. 26, 2013 and mailed May 7, 2013 (7 pgs.).
Final Rejection for U.S. Appl. No. 14/098,434, dated Mar. 2, 2016, 17 pages.
Office action for U.S. Appl. No. 14/098,434, dated Sep. 25, 2015, 11 pages.

* cited by examiner

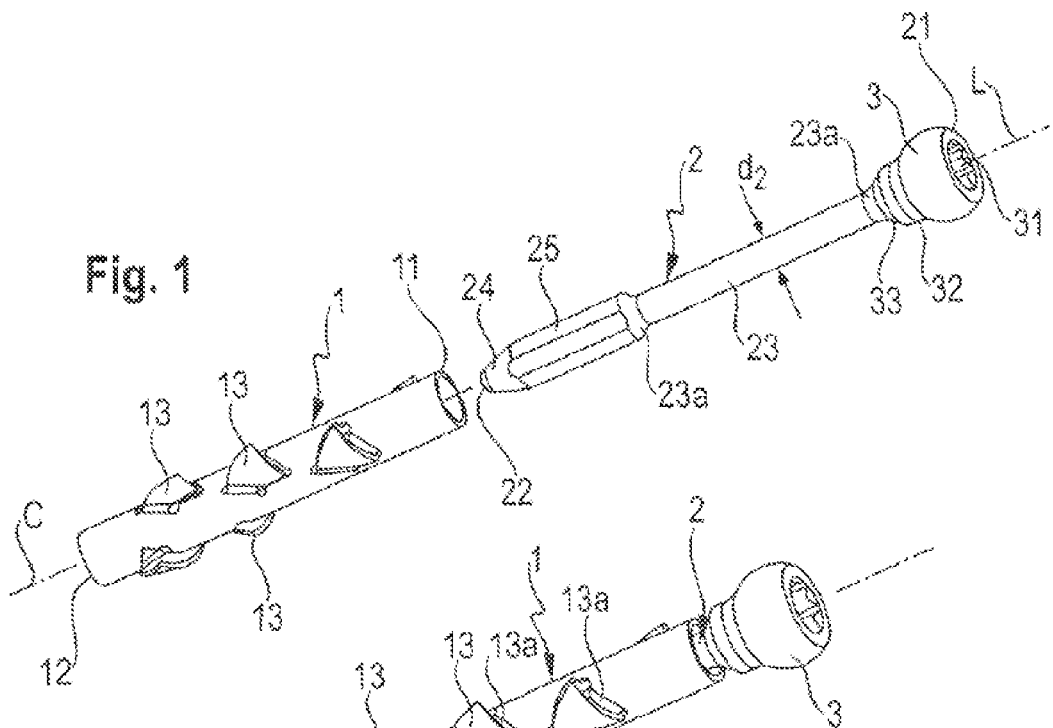
Fig. 1
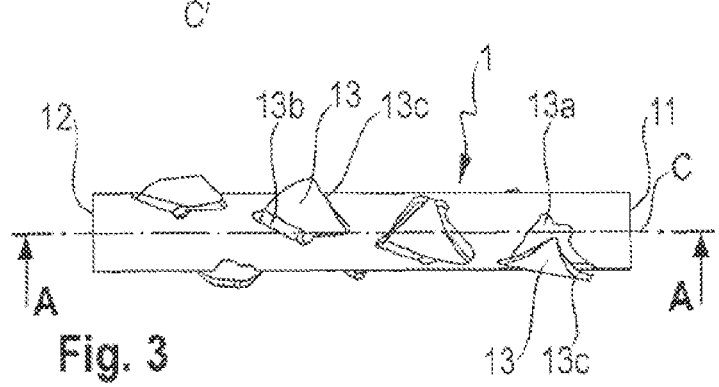
Fig. 2
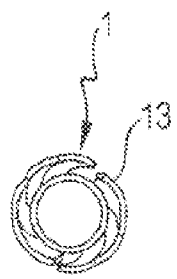
Fig. 5
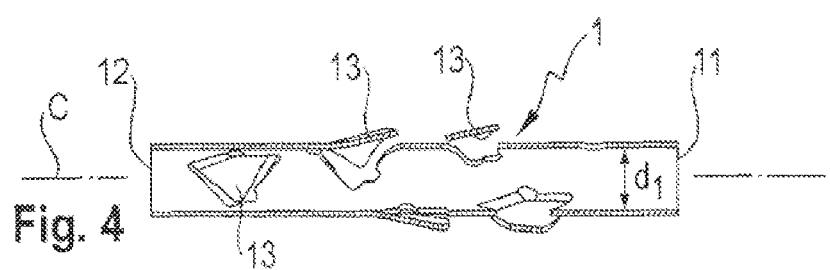
Fig. 3
Fig. 4

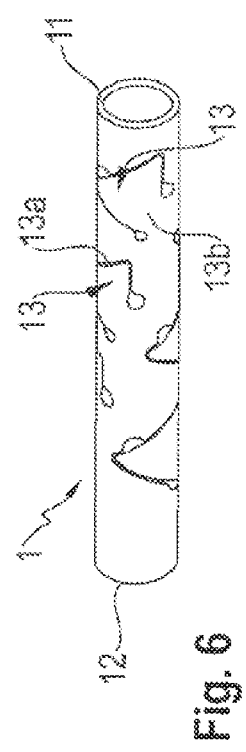
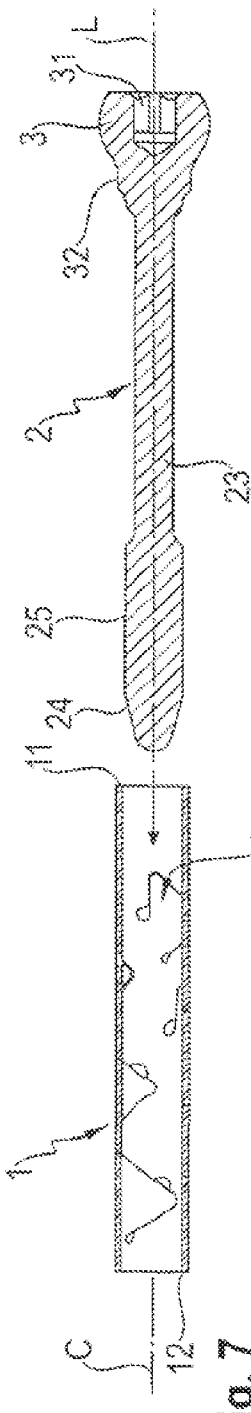
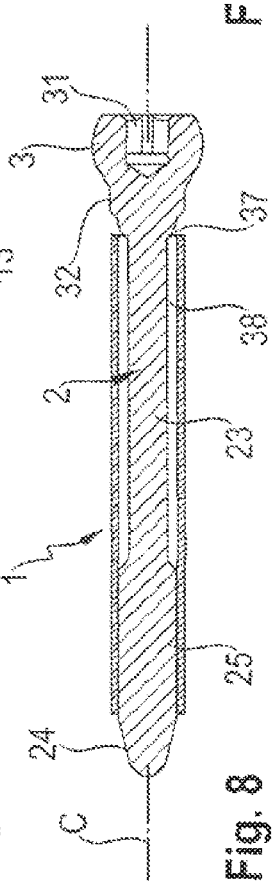
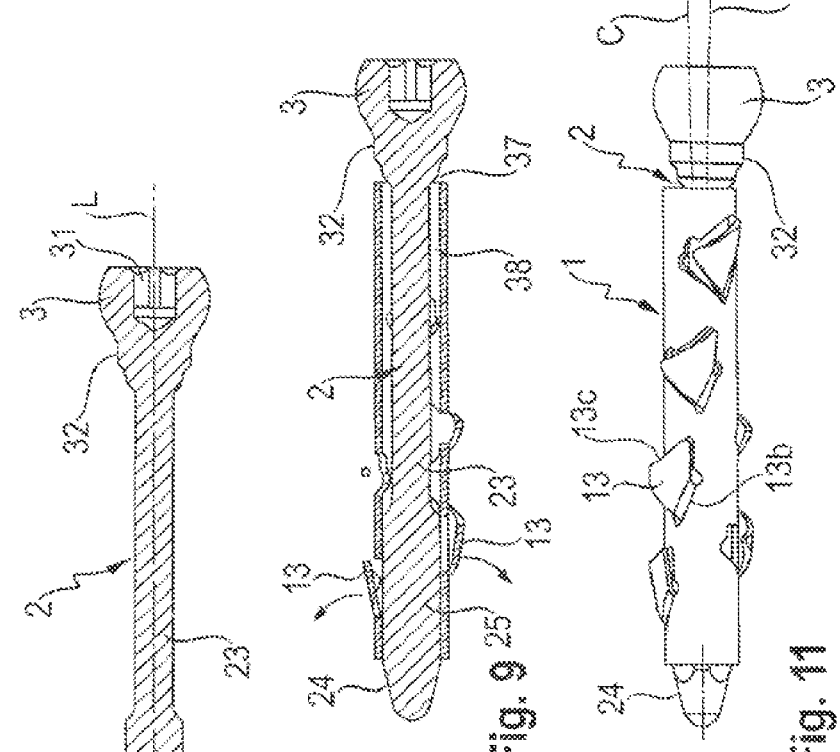
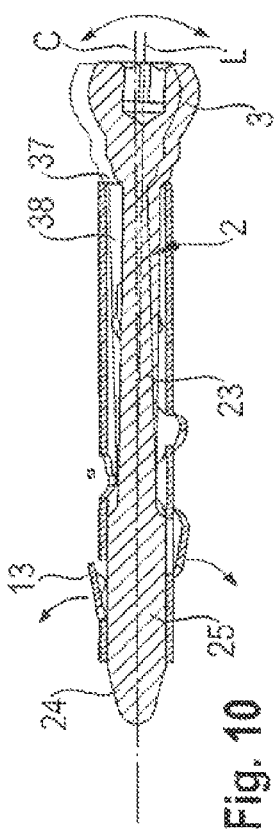
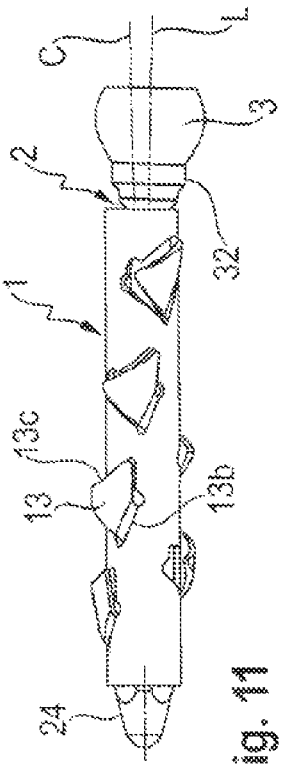

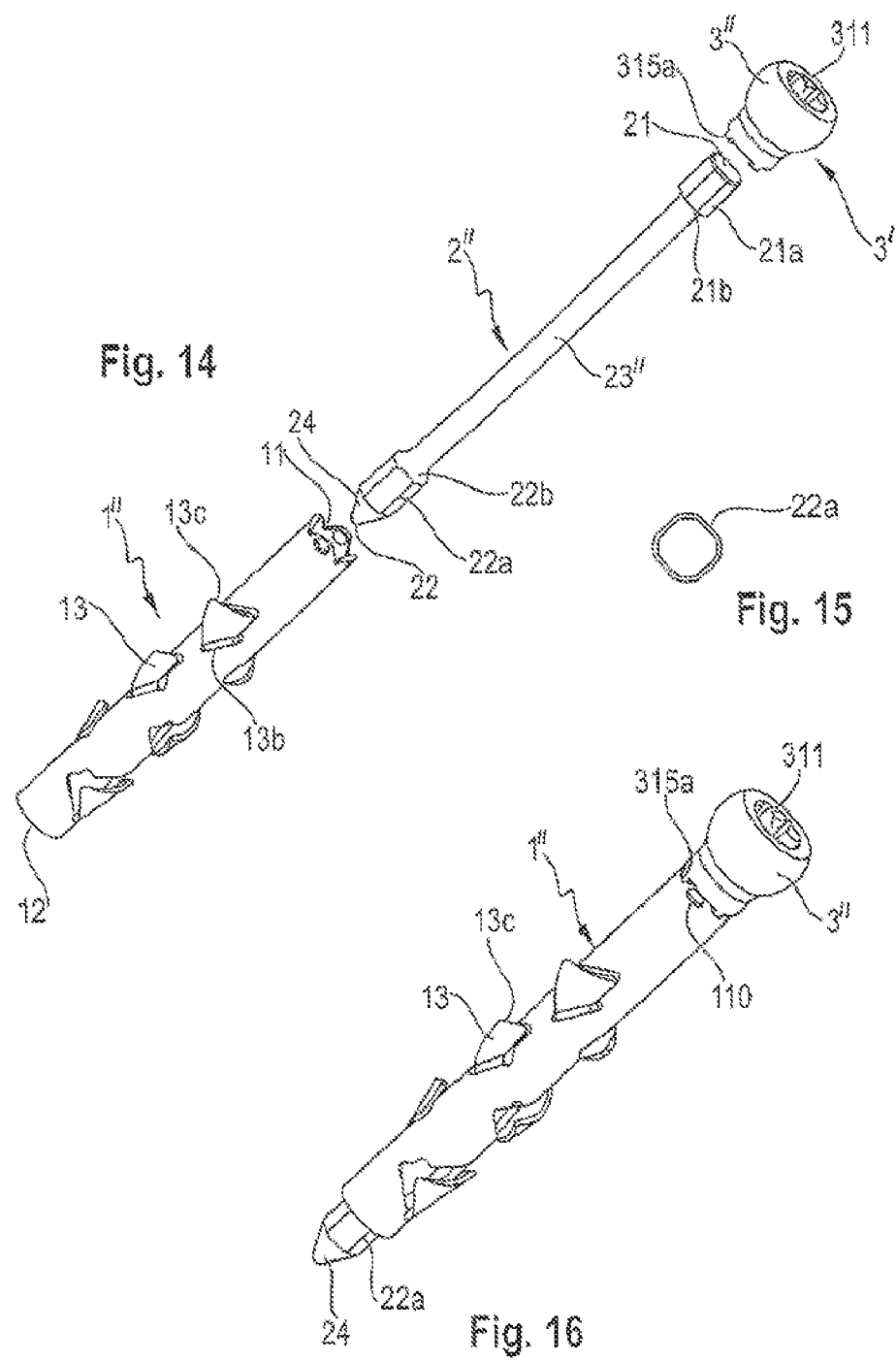

DYNAMIC BONE ANCHOR AND METHOD OF MANUFACTURING A DYNAMIC BONE ANCHOR

CROSS-REFERENCE TO RELATED APPLICATION

This application is a continuation of U.S. patent application Ser. No. 14/098,425, filed Dec. 5, 2013, no U.S. Pat. No. 11,045,237, which claims priority to and the benefit of U.S. Provisional Application No. 61/733,793, filed on Dec. 5, 2012, in the U.S. Patent and Trademark Office, the entire content of which is incorporated herein by reference; and claims priority from European Patent Application EP 12 195 759.1, filed Dec. 5, 2012, the entire content of which is incorporated herein by reference.

BACKGROUND

1. Field

The invention relates to a dynamic bone anchor and a method of manufacturing a dynamic bone anchor. The dynamic bone anchor comprises an anchor member for anchoring to a bone or vertebra, and a longitudinal core member provided in the anchor member. A portion of the anchor member is movable relative to the core member. The anchor member is made at least partially of a material that comprises a nickel-titanium (Ni—Ti) based shape memory alloy having superelastic properties. The dynamic bone anchor is particularly applicable in the field of dynamic bone fixation or dynamic stabilization of the spinal column in cases of osteoporotic or weak bones.

2. Description of the Related Art

A bone anchoring element comprising a tubular body provided with a plurality of barb elements wherein the barb elements are arranged along at least one helical line around the central axis of the tubular body is known from U.S. Pat. No. 8,292,932 B2. The tubular body can be made of a shape memory alloy having shape memory and/or superelastic characteristics, in particular, Nitinol. The bone anchoring element further includes an essentially cylindrical shaft inside the tubular body and a head that is connected to the tubular body by a form-fit connection preventing said tubular body from rotating relative to the cylindrical shaft part. Hence, the head is fixed to the tubular body during use of the bone anchoring element.

A dynamic bone fixation element is known from US 2009/0157123 A1, which includes a bone engaging component and a load carrier engaging component. The bone engaging component includes a plurality of threads for engaging a patient's bone and a lumen. The load carrier has a shaft portion that at least partially extends into the lumen. The distal end of the shaft portion is coupled to the lumen and at least a portion of an outer surface of the shaft portion is spaced away from at least a portion of an inner surface of the lumen via a gap so that a head portion can move with respect to the bone engaging component.

SUMMARY

It is the object of the invention to provide a dynamic bone anchor that is particularly suitable for weak and/or osteoporotic bones or vertebrae. Further, a method of manufacturing such a dynamic bone anchor shall be provided.

With the dynamic bone anchor, bone parts or vertebrae to be fixed or stabilized are able to carry out a controlled limited motion relative to each other. An anchor member of the bone anchor is preferably made of a Ni—Ti based shape memory alloy that is in the superelastic metallurgical state under the conditions in which the bone anchor is used in a patient.

Superelasticity, sometimes called pseudoelasticity, involves the creation of stress-induced martensite which simultaneously undergoes strain when it is formed to release the applied stress. When the applied stress is released, the thermally unstable martensite reverts to austenite, and the strain returns to zero. This process results in high elasticity in the material.

The bone anchor is of the type of a push-and-turn anchor, meaning, it can be pressed into a prepared core hole in a bone while the barb elements on the outer surface of the anchor member are collapsed. Because the barb elements provide a thread-like function, the position of the bone anchoring element in the core hole can be corrected after inserting the bone anchor into the core hole, by either positioning it deeper into the bone by means of a screwing-inwards motion or by screwing it backward to position it more shallowly. The push-and-turn anchor is particularly useful for weak and/or osteoporotic bones.

Because the barb elements project outward once the anchor member is inserted into a bone, the bone anchor is prevented from being pulled out or coming loose. The bone anchor can be removed, if required, like a screw by turning it in the opposite, for example counter-clockwise, direction from which it was inserted.

The anchor member exhibits superelastic behavior once it is inserted into the bone. Therefore, it can be slightly deformed, in particular it can be deflected from its original anchor axis. Therefore, a head that is connected to the core member can perform a limited rotational and/or translational movement relative to the anchor axis. Due to the superelastic behavior of the anchor member, the extent of possible movement of the anchor member relative to the core member is increased compared to materials without superelasticity.

In one embodiment, the head that is connected to the core member is movable with respect to the anchor member in a limited manner only when the bone anchor has been inserted in the bone. In this case, the core member is also made of material comprising a Ni—Ti shape memory alloy, in particular Nitinol, so that the core member deforms once it is inserted with the anchor member into the bone, releasing the fixation between the anchor member and the head.

A method of manufacturing the bone anchor makes use of the shape memory effect of the Ni—Ti shape memory alloy of the anchor member. The barb elements are deployed and the anchor member is in the superelastic state in a temperature range that includes body temperature. The anchor member may be brought into this state by shape setting. Through cooling and deforming the anchor member, the barb elements are impressed and allow an easy insertion of the bone anchor into a core hole. The core member can be easily inserted into the anchor member in this configuration. Upon heating, the core member is connected to the anchor member by a strong press-fit connection. Finally, the barb elements are deployed and provide anchoring to the bone.

Due to the superelastic behaviour of the anchor member, the degree of possible movement of the anchor member relative to the core member is increased compared to materials without superelasticity.

BRIEF DESCRIPTION OF THE DRAWINGS

Further features and advantages of the invention will become apparent from the description of embodiments by means of the accompanying drawings. In the drawings:

FIG. 1 shows a perspective exploded view of a dynamic bone anchor according to a first embodiment.

FIG. 2 shows a perspective view of the dynamic bone anchor of FIG. 1 in an assembled state.

FIG. 3 shows a side view of the anchor member of the dynamic bone anchor according to the first embodiment.

FIG. 4 shows a cross-sectional view of the anchor member along line A-A of FIG. 3.

FIG. 5 shows a top view along the anchor axis of the anchor member shown in FIGS. 1 to 3.

FIG. 6 shows a perspective view of the anchor member with barb elements in a deformed condition, wherein the barb elements are substantially flush with the outer surface of the anchor member.

FIG. 7 shows a cross-sectional view of a step of manufacturing the bone anchor according to the first embodiment, the cross-section taken in a plane containing the anchor axis.

FIG. 8 shows a cross-sectional view of a step of manufacturing the bone anchor according to the first embodiment, where the core member has been inserted into the anchor member.

FIG. 9 shows a cross-sectional view of a step of using the bone anchor according to the first embodiment, wherein the barb elements are splayed outwards.

FIG. 10 shows a cross-sectional view of the bone anchor according to the first embodiment, wherein the anchor member is deformed and, as a consequence, the core member and head perform a relative movement with respect to the anchor member.

FIG. 11 shows a side view of the bone anchor according to FIG. 10.

FIG. 14 shows a perspective exploded view of a dynamic bone anchor according to a second embodiment.

FIG. 15 shows a schematic view of the outer contour of a connection portion of the core member of the dynamic bone anchor according to FIG. 14.

FIG. 16 shows a perspective view of the dynamic bone anchor according to the second embodiment in an assembled state.

DETAILED DESCRIPTION

Figure 12:
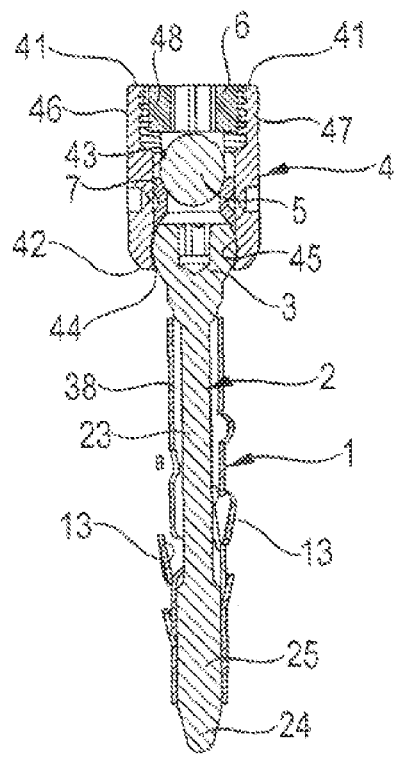
FIG. 12 shows a cross-sectional view of a polyaxial pedicle screw using the dynamic bone anchor according to the first embodiment as an anchoring element.

As shown in FIGS. 1 and 2, a dynamic bone anchor according to a first embodiment comprises an anchor member 1 in the form of a tubular body, and a longitudinal core member 2 that can be inserted into the anchor member 1 and connected thereto to form the bone anchor.

Referring to FIGS. 3 to 5, the anchor member 1 comprises a first end 11 and an opposite second end 12. The tubular body 1 has the shape of a substantially cylindrical tube with a cylinder axis C. An inner diameter $d_1$ and a length of the tubular body 1 are adapted to accommodate a portion of the core member 2 therein, as described below. At least a portion of an outer surface of the anchor member 1 is provided with a plurality of barb elements 13. The barb elements 13 are formed by cuts 13a made in a wall of the tubular body 1. Each of the cuts 13a comprises an end base 13b that is not cut out from the tubular body 1 and acts as an attachment and a bending side for the barb elements 13 in the wall of the tubular body 1. As can be seen in particular in FIG. 3, in a side view of the tubular member 1, the barb elements 13 have the contour of an irregular quadrangle with a free end 13c opposite to the base 13b and an inclination towards the base 13b. The inclination is such that the free ends 13c of the barb elements 13 form a helical line around the cylinder axis C of the tubular body 1. Hence, the barb elements 13 are arranged such that free ends 13c, or at least a portion thereof, form cutting edges similar to a crest of a screw thread.

As can be seen in particular in FIGS. 4 and 5, the barb elements 13 project from the outer surface of the tubular body 1 by an angle that is selected during the manufacturing process based upon the material used and the actual dimensions of the barb elements 13 to obtain a desired stiffness of the barb elements 13. Due to their configuration and attachment onto the wall of the tubular body 1, the barb elements 13 are elastically deformable relative to the tubular body 1. When the barb elements 13 are collapsed or pressed into the cuts 13a, they are pre-tensioned.

The anchor member 1 is made of a material that is based of a nickel-titanium shape memory alloy, preferably from Nitinol. The material exhibits superelasticity. Superelasticity is present in the austenitic metallurgical state. In particular, superelasticity is present in a temperature range slightly above the stress-free martensite to austenite transitioned temperature. This should be the temperature range of use including the body temperature. More preferably, the anchor member 1 is made of a nickel-titanium based shape memory alloy of the ELI (Extra Low Interstitial) type, in particular Nitinol of the ELI type. Such a material is of high purity and comprises, in particular, less oxygen compared to other Nitinol alloys that are not of the ELI type. For example, the oxygen content is less than 0.025 wt %, preferably equal to or less than 0.010 wt %, and more preferably, equal to or less than 0.005 wt %. The material has a fatigue strength limit that can be up to two times higher than that of other shape memory alloys not of the ELI type.

The core member 2 will now be described with reference to FIG. 1. The core member 2 comprises a first end 21 and an opposite second end 22. A longitudinal axis L extends through the core member 2 and is coaxial with cylinder axis C of the anchor member when the anchor member 1 and the core member 2 are not deflected with respect to each other. Adjacent to the first end 21, there is a head portion 3 that has a spherical segment shape. At the first end 21, a recess 31 for engagement with a tool for inserting the bone anchor is provided. Adjacent to the head 3, in the direction of the second end 22, there is a neck portion 32 that may be cylindrical, and adjacent to the neck portion 32, a section 33 with a diminishing outer diameter may be provided. A central portion 23 of the core member 2 is substantially rod-shaped and has a circular cross-section with an outer diameter $d_2$ that is smaller than the inner diameter $d_1$ of the tubular body of the anchor member 1. At the second end 22, there is a tip portion 24 which is followed by a connection portion 25 in a direction towards the central portion 23. The central portion 23 may extend over with slanted portions 23a with increasing diameter into the connection portion 25 and the neck portions 33, 32, respectively. The connection portion 25 has an outer contour of a square with rounded edges. The size of the connection portion 25 in a radial direction is such that the connection portion 25 can be connected in a press-fit manner in the tubular body of the anchor member 1, as explained below. The connection portion 25 further has a length in an axial direction adapted to provide sufficient fixation in the tubular body of the anchor member 1. A total length of the core member 2 is such that when the core member 2 is inserted into the anchor member 1, the tip portion 24 projects out of the second end 12 of the anchor member 1, and at least the neck portion 32 and the head 3 project out of the first end 11 of the anchor member 1, having a distance or gap 37 (FIG. 9) from the first end 11. It should be noted that the core member 2 may have a different design as regards the specific sequence and size of the different portions. However the size of the core member 2 should be such that the core member 2 is connectable to the anchor member 1 with at least a portion of the core member 2 while another portion of the core member 2 is free, such that the anchor member 1 is movable relative to the core member 2.

The core member 2 of this embodiment is made of a material that has a higher modulus of elasticity compared to a modulus of elasticity of the material of the anchor member 1, meaning that the core member 2 is made of a stiffer material than the anchor member 1. Preferably, the core member 2 is made of titanium or stainless steel. The core member 2 can also be made of a bio-compatible polymer material, provided that the dimensions, such as the length and the thickness of the core member 2, are such that the core member 2 does not have flexible behavior when it is inserted into a bone.

In FIGS. 6 and 7, steps of manufacturing the dynamic bone anchor according to the first embodiment are shown. The anchor member 1 is made from a tube in which the contours of the barb elements 13 are cut, for example, by laser cutting. In a shape setting procedure (a result of which is shown in FIG. 4), the barb elements 13 are bent outward and constrained in a fixture, and then the anchor member 1 is subjected to a heat treatment in order to define its shape as the final shape which the anchor member 1 assumes in the austenitic state exhibiting superelasticity. Thereafter, the anchor member 1 is subjected to cooling below the martensite finish temperature $M_f$ such that a phase transition of the material into the martensitic state takes place. Finally, a deforming process involving the task of moving the barb elements 13 back into the cuts 13a so that the anchor member 1 is in the deformed martensitic state, as shown in FIG. 6, may be performed.

Thereafter, referring to FIG. 7, the core member 2 is introduced with its tip portion 24 from the first end 11 of the anchor member 1 into the tubular body until the tip portion 24 projects out of the second end 12, as shown in FIG. 8. The radial size of the connection portion 25 is slightly oversized with respect to the inner diameter $d_1$ of the anchor member and the anchor member 1 is easily deformed in the martensitic state, a press-fit connection, in particular a distortion-fit connection, can be achieved between the connection portion 25 and the tubular body 1. The press-fit connection may become stronger after the application of heat, when the anchor member 1 assumes its pre-set shape. As shown in FIG. 8, the head 3 with the neck portion 32 and the intermediate portion 33 projects out of the first end 11 of the anchor member 1 when the core member 2 is fully inserted into and connected to the anchor member 1. Furthermore there is a gap 37 between the neck portion 32 and the anchor member 1, and a gap 38 between the central portion 23 and the inner wall of the anchor member 1.

In the configuration shown in FIG. 8, the anchor member 1 can be easily introduced into a core hole prepared in a bone part or a vertebra.

In use, first a core hole is prepared in the bone part or vertebra. Then, the bone anchor is inserted into the core hole in the collapsed state of the barb elements 13, as shown in FIG. 8. After heating the bone anchor, either through the heat of a receiving patient's body or by application of a heating device, the barb elements 13 splay outward from the tubular body as shown in FIG. 9. Even with no cooling, the barb elements 13 easily deform, allowing insertion of the anchor member 1 at low force. When the barb elements 13 project outward from the tubular body, they provide a thread-like function, which allows for correction of the position of the bone anchoring element in the core hole after inserting it into the core hole, by either positioning it deeper into the bone by means of a screwing-inwards motion or by screwing it backward to position it more shallowly. Furthermore, the barb elements 13 prevent the bone anchoring element from being pulled out or coming loose. The bone anchoring element can be removed, if required, like a screw, by turning it in the opposite or counter-clockwise direction from which it was inserted.

As can be seen in FIGS. 10 and 11, due to the superelasticity of the anchor member 1, the anchor member 1 may be deflected or deformed with respect to the longitudinal axis L of the core member 2, so that the anchor member 1 can perform a limited movement relative to the core member 2. The deflection takes place in a region near the connection portion 25 up to the first end 11 of the tubular body.

The motion of the anchor member 1 relative to the head 3 is limited by the abutment of an inner wall of the anchor member 1 against the core member 2. The extent of deflection of the anchor member 1 relative to the core member 2 depends on the elasticity of the material of the anchor member 1 and also of the size of the gaps 37, 38, meaning, on the thickness and the length of the core member 2. Due to the superelasticity of the material of the anchor member 1, the anchor member 1 may be shorter compared to an anchor member made of another metallic material.

A first application of the bone anchor together with a stabilization device is shown in FIG. 12. The bone anchor according to the first embodiment is coupled to a receiving part 4 to form a polyaxial bone anchor. The receiving part 4 is substantially cylindrical and comprises a top end 41, a bottom end 42, and a coaxial bore 43 extending from the top end 41 to a distance from the bottom end 42. The bore 43 narrows towards the bottom end 42 and provides an opening 44 near the bottom end 42. Near the opening 44, a seat 45 is provided for pivotably receiving the head 3. A U-shaped recess extends from the top end 41 to a distance from the top end 41 for receiving a stabilization rod 5. The U-shaped recess has two free legs 46, 47 which each have an internal thread 48 for cooperating with a locking member 6, such as a set screw. Furthermore, a pressure member 7 is provided that exerts pressure onto the head 3 such that the head 3 can be locked in a certain angular position by tightening the locking member 6. The bone anchor may be used with other designs of receiving parts and polyaxial bone screws. Also, the head 3 of the core member 2 may be designed such that it comprises a section for receiving a rod and for receiving a locking member to fix the rod as known from other monoaxial bone screws. In use, at least two polyaxial bone anchors are inserted into adjacent vertebrae or bone parts and connected via the rod 5. Once the anchor members 1 are inserted into the bone parts or adjacent vertebrae, the anchor members 1 can perform a limited motion with respect to the core members 2, respectively. Once a head 3 is locked in the receiving part 4, the bone anchor provides for a dynamic stabilization that allows small movements of the bone parts with respect to each other or small movements of a motion segment of the spinal column.

Figure 13:
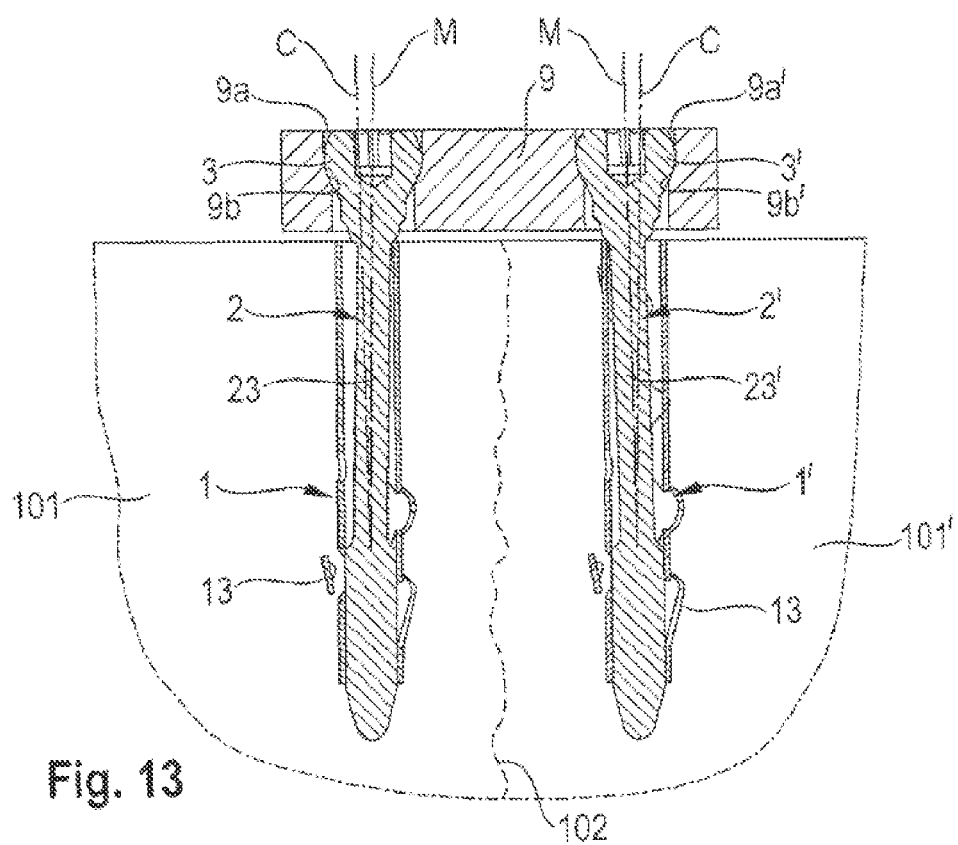
FIG. 13 shows a cross-sectional view of the dynamic bone anchor according to the first embodiment used with a bone plate.

A second example of application is shown in FIG. 13, wherein bone anchors according to the first embodiment are used together with a bone plate 9 comprising holes 9a, 9a' with seat portions 9b, 9b' for receiving the heads 3, 3' of the two bone anchors respectively. The two anchor members 1, 1' with core members 2, 2' are inserted in adjacent bone parts 101, 101', with the bone plate 9 bridging at least a portion of a fracture site 102. In the specific application, a distance between the center axes M of two holes 9a, 9a' that accommodate the heads 3, 3' of the bone anchors is slightly smaller than the distance between the longitudinal axes C of the anchor members 1, 1'. Because the anchor members 1, 1' can be deflected or deformed with respect to a longitudinal axis L of the respective core member 2, 2' (FIG. 10) in a direction transverse to the respective longitudinal axis C to allow the anchor member 1, 1' to perform a limited movement relative to the core member 2, the bone parts 101, 101' can be drawn together at the fracture site 102 as shown in FIG. 13.

A second embodiment of the bone anchor will be explained with reference to FIGS. 14 to 27. As shown in FIGS. 14 to 16, a dynamic bone anchor according to the second embodiment includes an anchor member 1", a core member 2" and a head 3". The core member 2" can be inserted into and connected to the anchor member 1", and the head 3" can be connected to the core member 2".

Figure 17:
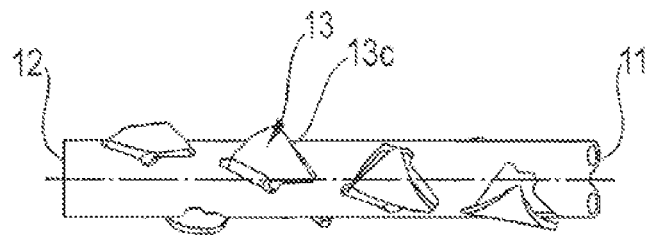
FIG. 17 shows a side view of the anchor member of the bone anchor according to the second embodiment in a state in which the barb elements are splayed outwards.
Figure 18:
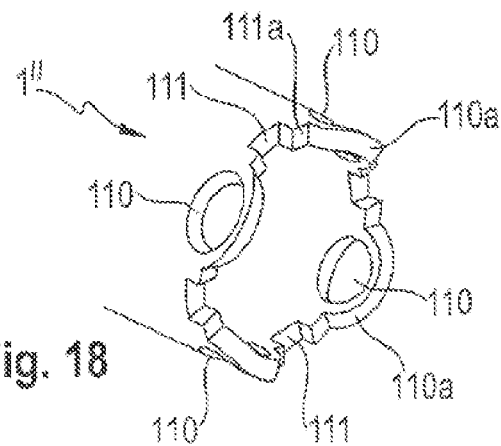
FIG. 18 shows an enlarged perspective view of an end portion of the anchor member according to FIG. 17.

Referring in particular to FIGS. 17 and 18 the anchor member 1" differs from the anchor member 1 of the first embodiment in the design of the edge portion of the first end 11. All other portions are the same or similar to that of the first embodiment and are indicated with the same reference numerals. The description thereof will not be repeated. The edge portion adjacent to the first end 11 comprises a plurality of substantially circular holes 110, for example, in the embodiment, four holes are formed in the wall of the tubular body 1", the holes 110 being arranged at a circumferential distance of 90° from each other around the cylinder axis C. An outer edge 110a of the holes 110 that forms the first end 11 of the anchor 1" is rounded. Between the holes 110, there are substantially rectangular recesses 111 open to the first end with substantially flat rims 111a at both sides of each open recess 111 that extend over into the rounded edges 110a of the holes 110. The rounded edges 110a project farther outward in an axial direction than the flat rims 111a so that the rounded edges 110a form the free end of the tubular body 1".

Referring in particular to FIGS. 14 and 15, the core member 2" is a longitudinal member comprising a first end 21, an opposite second end 22, and a substantially rod-shaped central portion 23". The central portion 23" has a circular cross-section with an outer diameter $d_2$ that is smaller than the inner diameter $d_1$ of the tubular body of the anchor member 1". Adjacent to the first end 21, there is a first connection portion 21a, and adjacent to the second end 22, there is a tip portion 24, as in the first embodiment. Following the tip portion 24, there is a second connection portion 22a. Each of the connection portions 21a, 22a has the outer contour of a square with rounded edges. The connection portion 22a is slightly oversized with respect to the inner diameter $d_1$ of the tubular body of the anchor member 1", so that it can be connected in a press-fit manner to the tubular body 1". As in the first embodiment, transition portions 21b, 22b, with increasing outer diameters toward their respective connection portion 21a, 22a, are provided between the central portion 23" and the first and second connection portions 21a, 22a, respectively.

In this embodiment, the core member 2" is also made of a material that is based on a nickel-titanium shape memory alloy, preferably from Nitinol, that exhibits superelasticity in the temperature range of use including the body temperature. Preferably, the core member 2" is made of the same material as the anchor member 1", however, the core member 2" might also be of a different nickel-titanium based shape memory alloy. In particular, the anchor member 1" and the core member 2" are made of the same Nitinol of the ELI type material as described previously in connection with the first embodiment.

Figures 19, 20:
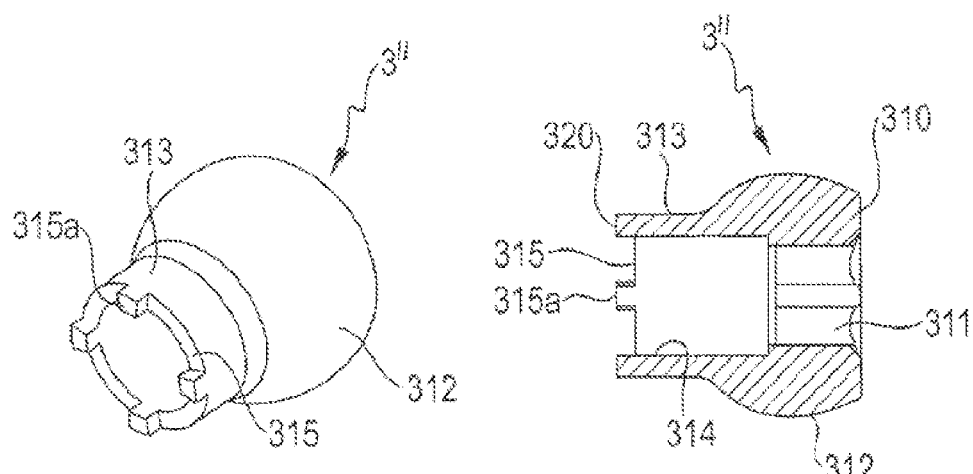
FIG. 19 shows a perspective view of a head of the dynamic bone anchor according to the second embodiment.
FIG. 20 shows a cross-sectional view of the head shown in FIG. 19, the cross-section taken in a plane containing the anchor axis.

Referring to FIGS. 19 and 20, the head 3" comprises a first end 310, an opposite second end 320, a recess 311 at the surface of the first end 310 for engagement with a tool, and a spherical segment-shaped portion 312 adjacent to the first end 310. Between the spherical-segment shaped portion 312 and the second end 320, there is a cylindrical neck portion 313 with a coaxial cylindrical recess 314 for accommodating the first connection portion 21a of the core member 2". The length and the inner diameter of the recess 314 is such that the first connection portion 21a can be accommodated therein with a press-fit connection.

The head 3" is preferably made of a material that is stiffer compared to the material of the core member 2" and the anchor member 1". Preferably, the head 3" is made of titanium or stainless steel.

An edge of the head 3" at the second end 320 comprises a plurality of circumferentially extending substantially rectangular recesses 315. In the embodiment, four recesses 315 that are spaced apart 90° from each other in a circumferential direction are provided. By means of this, four projections 315a are formed. The recesses 315 and the projections 315a formed thereby are adapted to mate the corresponding structure at the first end 11 of the tubular body of the anchor member 1″. In particular, the projections 315*a* fit into the recesses 111. The rounded edges 110*a* of the holes 110 fit into the recesses 315 when they are deformed such that the holes 110 are no longer circular, but flattened. When the projections 315*a* extend into the recesses 111 of the tubular body of the anchor member 1″ and the rounded edges 110*a* are deformed in a direction towards the second end 12, a form-fit connection between the head 3″ and the anchor member 1″ is established, such as shown, for example, in FIGS. 22 and 23. By means of the form-fit connection, the head 3″ is prevented from moving, and from rotating relative to the anchor member 1″.

Figure 21:
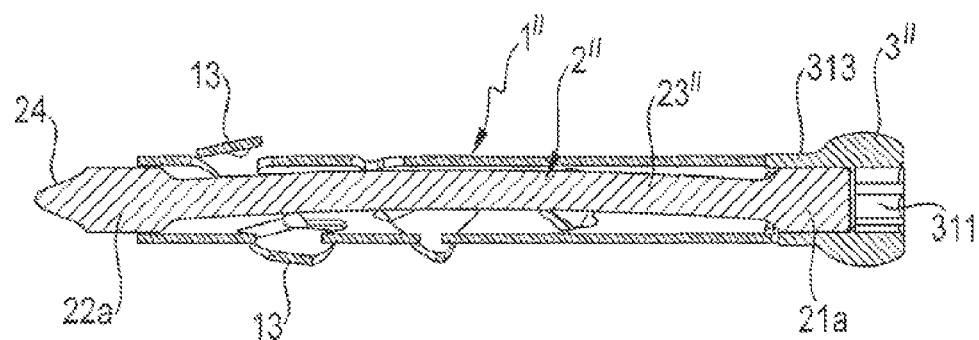
FIG. 21 shows a cross-sectional view of the bone anchor according to the second embodiment with the head fixed to the anchor member.
Figure 22:
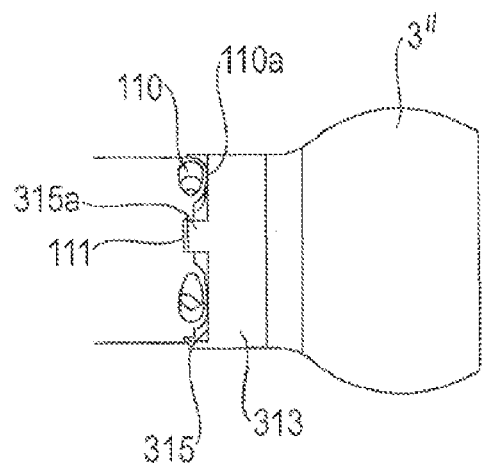
FIG. 22 shows an enlarged side view of a portion of the bone anchor according to FIG. 21 depicting a detail of the connection between the head and the anchor member.
Figure 23:
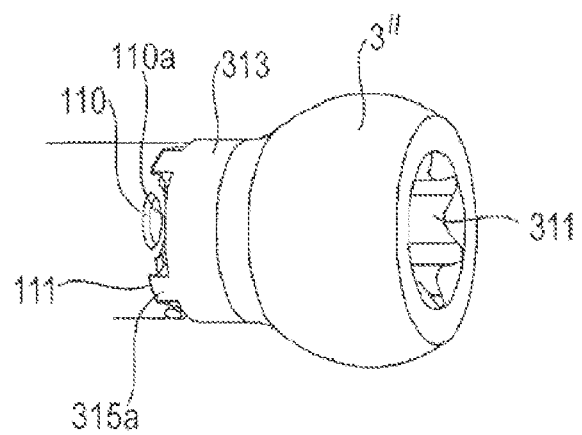
FIG. 23 shows an enlarged perspective view of a portion of the dynamic bone anchor depicted in FIG. 21.

The bone anchor according to the second embodiment is manufactured as follows. First, the tubular body of the anchor member 1″ is formed into the shape it assumes in the high temperature austenitic phase by means of, for example, shape setting. In this final shape, the barb elements 13 are splayed out, and the holes 110 have a substantially circular cross-section. Then, the anchor member 1″ is cooled and deformed so that the material performs a phase transition into the martensitic state. The barb elements 13 are pressed into the cuts 13*a*, and the rounded edges 110*a* of the holes 110 become deformable. The core member 2″, as shown in FIG. 21, may be pre-assembled with the head 3″, cooled, and deformed such that the central portion 23″ is bent away from the cylinder axis C. Accordingly, the length of the core member 2″ is decreased. Then, the core member 2″ with the bent central portion 23″ and the pre-assembled head 3″ is inserted into the anchor member 1″ as shown in FIGS. 21 to 23, until the projections 315*a* fit into the recesses 111, so that a form-fit connection is established between the head 3″ and the anchor member 1″. By inserting the projection 315*a* into the recesses 111, the recesses 315 press onto the rounded edges 110*a* of the holes 110, and deform the holes 110.

Figure 24:
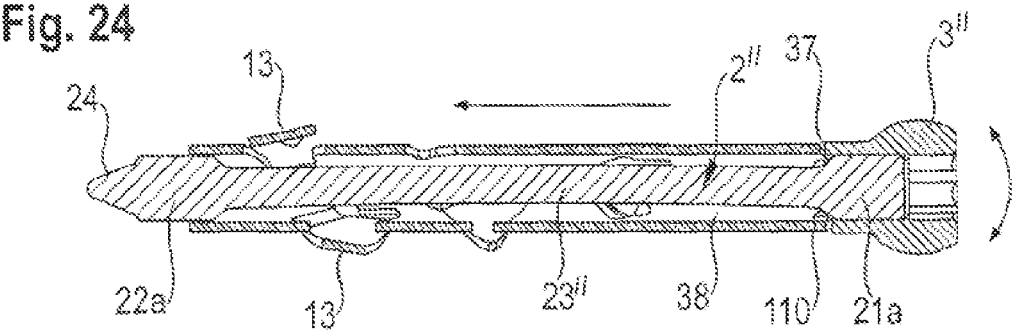
FIG. 24 shows a cross-sectional view of the dynamic bone anchor according to the second embodiment in a state in which the head is disconnected from the anchor member and is movable relative thereto.
Figure 25:
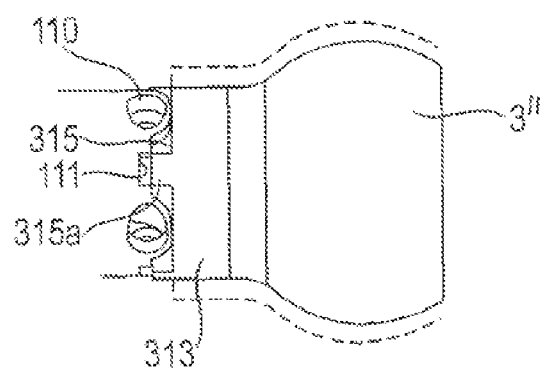
FIG. 25 shows an enlarged side view of a portion of the dynamic bone anchor shown in FIG. 24 illustrating the movement of the head relative to the anchor member.
Figure 26:
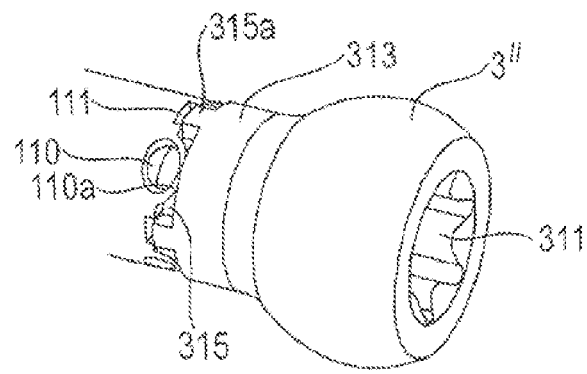
FIG. 26 shows an enlarged perspective view of a portion of FIG. 24 showing the detail of the arrangement of the head relative to the anchor member in the movable condition of the head.
Figure 27:
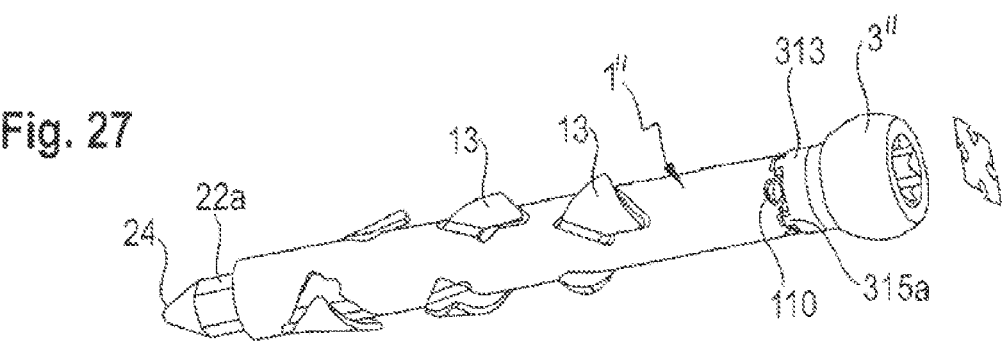
FIG. 27 shows a perspective view of the dynamic bone anchor according to the second embodiment in a state in which the head is movable relative to the anchor member.

The bone anchor manufactured in this manner can be inserted in this configuration into a core hole prepared in a bone or vertebra. Following the application of heat, for example through body heat or by means of a separate heating device, the anchor member 1″ and the core member 2″ assume their previously set shape. Hence, the barb elements 13 are splayed out and the core member 2″ returns from a bent shape into a less bent shape or into a substantially straight shape. By means of this, the rounded edges 110*a* that limit the holes 110 extend so that the holes 110 assume a circular shape. During this step, the rounded edges 110*a* press against the bottom of the recesses 315 of the head 3″ and the projections 315*a* are moved out of engagement with the recesses 111. The core member 2″ may remain only slightly bent as shown in FIG. 24. The form-fit connection between the head 3″ and the anchor member 1″ is released, and the head 3″ is movable with respect to the anchor member 1″, as shown in FIGS. 24 to 27. As can be seen in particular in FIGS. 25 and 26, the projections 315*a* may abut against the rounded edges 110*a*, thereby limiting a movement of the anchor member 1″ relative to the head 3″.

A still further straightening of the central portion 23″ of the core member 2″ may further push the head 3″ away from the anchor member 1″ so that the movement of the head 3″ is no longer limited by the rounded edges 110*a*, but only by an abutment of the core member 2″ against a portion of the inner wall of the tubular body of the anchor member 1″.

Further adaptations or modifications of the dynamic bone anchor described in the embodiments can be accomplished by one of ordinary skill in the art without departing from the scope of the invention. For example, the head may have any other shape suitable for connecting it to other stabilization devices such as bone plates, receiving parts for accommo-dating stabilization rods, etc. The head may even be omitted if the free end of the core member is suitable for connection to another device. In such a case, the free end of the core member may comprise an engagement portion for a driver. In both cases with or without a head or head portion, the drive portion of the bone anchor for engagement with a tool is at the end of the core member that is finally moveable with respect to the anchor member.

The structure of the second embodiment that includes the circular holes 110 and the recesses 315 may be different. Triangular holes or any other deformable structure may be utilized.

Any kinds of tips may be provided. The tips shown in the embodiment may even be omitted. For example, the hollow tubular anchor member according to the embodiments may have prongs at the second end 12.

The structure of the barb elements 13 may be different. The barb elements may have a trapezoidal shape, for example. Another bone engagement structure may be provided, for example a bone thread or a roughened surface.

The embodiments may also be combined among each other, only as an example for such a combination, the anchor member for the first embodiment may have a separate head, for example a titanium head, that is connected with the core member.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A dynamic bone anchor comprising:
an anchor member having a first end, a second end, and an anchor axis extending through the first and second ends, the anchor member comprising a tubular body with an inner surface defining a bore, the inner surface having a first inner width, and a bone engagement structure on at least a portion of an outer surface of the anchor member configured to engage a bone; and
a longitudinal core member having a first portion and a second portion, the second portion extending from the first portion and having a first outer width that defines a greatest outer width of the second portion, wherein the first outer width is greater than the first inner width of the tubular body when the core member is outside the tubular body;
wherein at a first temperature, the inner surface of the tubular body is deformable to increase the first inner width by insertion of the second portion of the core member into the tubular body while the first outer width of the second portion remains constant when inside the tubular body, and wherein at a second temperature greater than the first temperature, a radial force applied by the anchor member on the second portion of the core member is increased to strengthen a connection between the tubular body and the second portion of the core member;
wherein at a first position, the second portion of the core member is received in and fixed axially to the anchor member and contacts and deforms at least a first portion of the inner surface of the tubular body to have the increased first inner width, no part of the inner surface of the tubular body located between the first portion of the inner surface and the second end of the anchor member has an inner width that is less than the increased first inner width, the second portion of the core member and the anchor member are movable together, and the first portion of the core member and the anchor member are movable with respect to each other at the first end of the anchor member.

2. The dynamic bone anchor of claim 1, wherein the anchor member is made at least partially of a first material that comprises a nickel-titanium (Ni—Ti) based shape memory alloy.

3. The dynamic bone anchor of claim 1, wherein the second portion of the core member is fixed to the anchor member by a press-fit connection.

4. The dynamic bone anchor of claim 1, wherein the bone engagement structure comprises a thread-like structure configured to adjust a depth of the anchor member when engaging the bone.

5. The dynamic bone anchor of claim 4, wherein the thread-like structure is configured such that after insertion of the anchor member into a core hole, turning of the anchor member in a first direction is configured to cause the anchor member to be moved in an insertion direction deeper in the core hole, and turning of the anchor member in a second direction is configured to cause the anchor member to be moved in the core hole opposite to the insertion direction.

6. The dynamic bone anchor of claim 4, wherein the thread-like structure comprises a plurality of barb elements.

7. The dynamic bone anchor of claim 6, wherein each barb element is moveable between a first position adjacent to a surface of the tubular body and a second position farther from the surface of the tubular body than the first position of the respective barb element, and wherein at least a portion of a free cutting edge of each of the barb elements is inclined at an angle corresponding to a helical angle that extends for at least one full turn around the anchor axis.

8. The dynamic bone anchor of claim 1, wherein the first portion of the core member comprises a head.

9. The dynamic bone anchor of claim 1, wherein the core member further comprises a tip portion adjacent to the second portion.

10. The dynamic bone anchor of claim 9, wherein the tip portion is insertable into a first open end of the bore, and at the first position, the tip portion extends out of a second open end of the bore opposite the first open end.

11. A dynamic bone anchor comprising:
an anchor member having a first end, a second end, and an anchor axis extending through the first and second ends, the anchor member comprising a tubular body and a bone engagement structure on at least a portion of an outer surface of the anchor member configured to engage a bone, the tubular body comprising an inner surface defining a bore having an open first end corresponding to the first end of the anchor member and an opposite second end, wherein the anchor member is made at least partially of a first material that comprises a shape memory alloy having superelasticity;
a longitudinal core member having a first portion, a second portion, and an elongated shaft between the first and second portions, the second portion and the elongated shaft being insertable into the first end of the anchor member and moveable towards the second end of the anchor member, wherein the second portion defines a greatest outer width of any portion of the longitudinal core member that is insertable through the open first end of the bore;
wherein at a first position, the second portion of the core member is received in the bore with part of the second portion extending out of the second end of the bore, and the second portion is fixed axially to the anchor member by directly engaging a first portion of the inner surface adjacent to the second end of the bore, where a smallest diameter of the bore at the first portion of the inner surface is not less than a diameter of the open first end of the bore while the elongated shaft is spaced radially apart from the inner surface, and the core member does not have a surface at or adjacent to the second portion that faces the first portion of the core member against which any portion of the anchor member is configured to abut.

12. The dynamic bone anchor of claim 11, wherein the first material comprises a Ni—Ti based shape memory alloy.

13. The dynamic bone anchor of claim 11, wherein the second portion of the core member is fixed to the anchor member by a press-fit connection.

14. The dynamic bone anchor of claim 11, wherein the bone engagement structure comprises a thread-like structure configured to adjust a depth of the anchor member when engaging the bone.

15. The dynamic bone anchor of claim 14, wherein the thread-like structure is configured such that after insertion of the anchor member into a core hole, turning of the anchor member in a first direction is configured to cause the anchor member to be moved in an insertion direction deeper in the core hole, and turning of the anchor member in a second direction is configured to cause the anchor member to be moved in the core hole opposite to the insertion direction.

16. The dynamic bone anchor of claim 14, wherein the thread-like structure comprises a plurality of barb elements.

17. The dynamic bone anchor of claim 16, wherein each barb element is moveable between a first position adjacent to a surface of the tubular body and a second position farther from the surface of the tubular body than the first position of the respective barb element, and wherein at least a portion of a free cutting edge of each of the barb elements is inclined at an angle corresponding to a helical angle that extends for at least one full turn around the anchor axis.

18. The dynamic bone anchor of claim 11, wherein the first portion of the core member comprises a head.

19. The dynamic bone anchor of claim 11, wherein the core member further comprises a tip portion adjacent to the second portion.

20. The dynamic bone anchor of claim 19, wherein at the first position, the tip portion extends out of the second end of the bore.

* * * * *

UNITED STATES PATENT AND TRADEMARK OFFICE
CERTIFICATE OF CORRECTION

PATENT NO. : 11,896,275 B2
APPLICATION NO. : 17/334387
DATED : February 13, 2024
INVENTOR(S) : Lutz Biedermann et al.

Page 1 of 1

It is certified that error appears in the above-identified patent and that said Letters Patent is hereby corrected as shown below:

On the Title Page

Item (57), in Column 2, under "Abstract", Line 8, delete "number" and insert -- member --.

Item (57), in Column 2, under "Abstract", Line 9, delete "number" and insert -- member --.

In the Specification

In Column 1, Line 9, delete "no" and insert -- now --.

In the Claims

In Column 12, Line 12, in Claim 11, after "by" delete "directly".

Signed and Sealed this
Fourteenth Day of May, 2024

Katherine Kelly Vidal
*Director of the United States Patent and Trademark Office*